(12) United States Patent
Chow et al.

(10) Patent No.: US 8,586,085 B2
(45) Date of Patent: *Nov. 19, 2013

(54) METHODS AND FORMULATIONS FOR MAKING PHARMACEUTICAL COMPOSITIONS CONTAINING BUPROPION

(75) Inventors: San-Laung Chow, San Jose, CA (US); David Wong, Milpitas, CA (US); Damian Garcia, Sunnyvale, CA (US)

(73) Assignee: Biokey, Inc., Fremont, CA (US)

( * ) Notice: Subject to any disclaimer, the term of this patent is extended or adjusted under 35 U.S.C. 154(b) by 1744 days.

This patent is subject to a terminal disclaimer.

(21) Appl. No.: 11/265,918

(22) Filed: Nov. 3, 2005

(65) Prior Publication Data
US 2006/0099260 A1 May 11, 2006

Related U.S. Application Data

(60) Provisional application No. 60/626,317, filed on Nov. 8, 2004.

(51) Int. Cl.
*A61K 9/20* (2006.01)
*A61K 9/24* (2006.01)
*A61K 9/22* (2006.01)
*A61K 9/28* (2006.01)

(52) U.S. Cl.
USPC ............ 424/472; 424/464; 424/468; 424/474

(58) Field of Classification Search
None
See application file for complete search history.

(56) References Cited

U.S. PATENT DOCUMENTS

| | | | |
|---|---|---|---|
| 4,687,660 A | 8/1987 | Baker et al. | |
| 4,769,027 A | 9/1988 | Baker et al. | |
| 4,792,452 A * | 12/1988 | Howard et al. | 424/475 |
| 5,358,970 A | 10/1994 | Ruff et al. | |
| 5,427,798 A | 6/1995 | Ludwig et al. | |
| 5,541,231 A | 7/1996 | Ruff et al. | |
| 5,681,584 A | 10/1997 | Savastano et al. | |
| 5,731,000 A | 3/1998 | Ruff et al. | |
| 5,763,493 A | 6/1998 | Ruff et al. | |
| 5,952,005 A * | 9/1999 | Olsson et al. | 424/458 |
| 5,968,553 A | 10/1999 | Maitra et al. | |
| 6,033,686 A | 3/2000 | Seth | |
| 6,083,532 A | 7/2000 | Zhang et al. | |
| 6,096,341 A | 8/2000 | Seth | |
| 6,117,453 A | 9/2000 | Seth | |
| 6,120,803 A | 9/2000 | Wong et al. | |
| 6,143,327 A | 11/2000 | Seth | |
| 6,194,002 B1 | 2/2001 | Sherman | |
| 6,210,716 B1 | 4/2001 | Chen et al. | |
| 6,221,917 B1 | 4/2001 | Maitra et al. | |
| 6,238,697 B1 | 5/2001 | Kumar et al. | |
| 6,242,496 B1 | 6/2001 | Kulkarni et al. | |
| 6,251,430 B1 | 6/2001 | Zhang et al. | |
| 6,306,436 B1 | 10/2001 | Chungi et al. | |
| 6,333,332 B1 | 12/2001 | Han et al. | |
| 6,346,268 B1 | 2/2002 | Zhang et al. | |
| 6,350,471 B1 | 2/2002 | Seth | |
| 6,368,628 B1 | 4/2002 | Seth | |
| 6,462,237 B1 | 10/2002 | Gidwani et al. | |
| 6,485,748 B1 * | 11/2002 | Chen et al. | 424/482 |
| 6,589,553 B2 | 7/2003 | Li et al. | |
| 6,652,882 B1 | 11/2003 | Odidi et al. | |
| 2003/0134872 A1 * | 7/2003 | Asai et al. | 514/301 |
| 2004/0037883 A1 | 2/2004 | Zhou et al. | |
| 2004/0121010 A1 | 6/2004 | Hirsh et al. | |
| 2006/0099261 A1 * | 5/2006 | Chow et al. | 424/472 |
| 2006/0099262 A1 * | 5/2006 | Chow et al. | 424/472 |

FOREIGN PATENT DOCUMENTS

| | | |
|---|---|---|
| CN | 1352938 | 6/2002 |
| EP | 0171457 B1 | 3/1992 |
| WO | WO 00/50010 | 8/2000 |
| WO | WO 01/19346 A1 | 3/2001 |
| WO | WO 01/37808 | 5/2001 |

OTHER PUBLICATIONS

Ageeva et al. "The Selection of Moisture-Resistant Coatings for Tablets and Granules," Pharmaceutical Chemistry Journal, vol. 2, No. 10, 1968.*
Swarbrick, et al. Ed. "Encyclopedia of Pharmaceutical Technology," Second Edition, vol. 3, Marcel Dekker, Inc, 2002, p. 2649.*
PCT International Search Report, May 4, 2006.
Extended European Search Report, dated Jul. 23, 2008, for European Patent Application No. 05818240.3.
PCT International Search Report and Written Opinion dated Jun. 17, 2008 for International Application No. PCT/US2006/61625. (BIOK0010 PCT 02).
PCT International Search Report and Written Opinion dated May 4, 2006 for International Application No. PCT/US2005/40665. (BIOK/0010 PCT).
EPC Official Communication pursuant to Article 94(3) EPC dated Dec. 14, 2010 for Application No. 05818240.3 (BIOK/0010EPCX).
Notice of First Office Action dated Sep. 19, 2008 for Chinese Patent Application No. 200580037819.4. (BIOK/0010 CHIN P).

* cited by examiner

*Primary Examiner* — Rachael E Bredefeld
(74) *Attorney, Agent, or Firm* — Patterson & Sheridan, LLP

(57) ABSTRACT

Embodiments of the invention generally provide pharmaceutical drug compositions, methods of preparing oral drug compositions, such as extended release dosage compositions, and methods for treating antidepressant or smoking cessation. In one aspect, the invention provides a pharmaceutical formulation comprising a core, including bupropion and its salt derivatives, and a coating. The coating may include from about 5% to about 99% by weight of the coating of a pharmaceutically acceptable pH-independent polymer. The coating may further include from about 0.001% to about 30% by weight of the coating of a surfactant. In another aspect, the invention provides methods for preparing and administering a pharmaceutical composition in oral dosage form, such as a tablet.

9 Claims, No Drawings

METHODS AND FORMULATIONS FOR MAKING PHARMACEUTICAL COMPOSITIONS CONTAINING BUPROPION

CROSS-REFERENCE TO RELATED APPLICATIONS

This application claims benefit of U.S. provisional patent application Ser. No. 60/626,317, entitled, "METHODS AND FORMULATIONS FOR MAKING PHARMACEUTICAL COMPOSITIONS CONTAINING BUPROPION", filed Nov. 8, 2004, which is herein incorporated by reference.

BACKGROUND OF THE INVENTION

The invention generally relates to pharmaceutical compositions, such as drug formulations present in a solid form for oral administration. More particularly, the invention relates to long-lasting sustained dosage compositions, and carriers and active ingredients in the compositions thereof, such as extended release drug compositions for oral controlled release dosage formulations containing a drug and a carrier material.

Drug delivery at a predetermined rate such that drug concentrations can be maintained at desired therapeutically effective levels over an extended period, has received a great deal of attention. Many known solid drug formulations are required to be taken orally three or four times a day. There is a need for oral formulations to be taken less often, such as once per day. In addition, there are other problems with undesired drug delivery rate. For example, various side effects are observed for immediate release drug formulations due to high drug concentrations released in the plasma or blood stream right after the intake of the drug.

Bupropion is a commonly used as an antidepressant drug. It is generally formulated from its salt derivatives, such as its hydrochloride salts. A commercial example is Wellbutrin®. However, it has been shown that immediate release formulations of bupropion hydrochloride can induce some severe side effects, such as seizures, high blood pressure, and severe allergic reactions. There is a need to prepare a new sustained release dosage form to reduce side effect problems.

Various approaches exist for preparing sustained or controlled release pharmaceutical formulations, such as various extended release formulations in tablet or capsule form. For example, one method of forming delayed or sustained release formulations includes coating the tablet with a release-retarding coating, or coating individual granules with such a coating, and compressing these coated granules into a tablet. Exemplary techniques involving sustained release solid preparations for bupropion hydrochloride in a matrix are described in U.S. Pat. Nos. 5,358,970 and 5,427,798. However, bupropion hydrochloride is unstable and the use of a stabilizer as described in the above two patents to stabilize the drug make the matrix methods is not very well suited.

Another example involves controlled release tablet formulations for bupropion hydrochloride by using a core containing bupropion hydrochloride and a coating of a mixture having a water-insoluble/water-permeable film-forming polymer, a pore-forming agent, and other excipients, as described in U.S. Pat. No. 4,687,660 and EP-A-0171457. However, the pore-forming agent renders the coating of the core non-uniform and the release rate of the tablet not stable. Other examples of controlled release tablets, as described in U.S. Pat. Nos. 6,096,341 and 6,143,327, require a core and a first coating to prepare a delayed release table, the first coating including a water-insoluble/water-permeable film-forming polymer, a plasticizer, and a water-soluble polymer. A second coating or an immediate release coating is then coated onto the delayed release tablet.

Therefore, there is a need for an improved controlled release formulation and method for preparing such a controlled release formulation.

SUMMARY OF THE INVENTION

The invention generally provides a pharmaceutical composition having a therapeutically active agent, such as bupropion and its salts and derivatives thereof, prepared into a core. The pharmaceutical composition may include a coating outside the core. The coating may include a pharmaceutically acceptable pH-independent polymer and a surfactant.

In one aspect, an extended release pharmaceutical composition having a core of a pharmaceutical mixture and a coating layer is provided. The pharmaceutical mixture may include bupropion, such as about 10 mg to about 500 mg of bupropion hydrochloride, e.g., about 150 mg or about 300 mg. The coating layer may include a pharmaceutically acceptable pH-independent polymer, such as from about 5% to about 99% by weight of the coating of a pharmaceutically acceptable pH-independent polymer. The pharmaceutically acceptable coating mixture may further include a surfactant, such as from about 0.01% to about 30% by weight of the coating of a surfactant.

For example, a pharmaceutical composition may include bupropion or a salt thereof (e.g., hydrochloride salt derivative) at from about 5% to about 95% of its total weight. The pharmaceutical composition may further include a pharmaceutically acceptable pH-independent polymer at from about 0.01% to about 50% of it total weight and a surfactant at from about 0.001% to about 30% of its weight.

In another aspect, the invention further provides a method of preparing a pharmaceutical composition. The method includes forming a core having a pharmaceutical mixture and coating the core with a coating layer of a pharmaceutically acceptable coating mixture. The pharmaceutical acceptable coating mixture includes a pharmaceutically acceptable pH-independent polymer and a surfactant.

In addition, a method of administering a pharmaceutical composition is provided. The method includes administering to a mammal an effective amount of a pharmaceutical composition containing bupropion.

DETAILED DESCRIPTION OF THE INVENTION

The pharmaceutical composition of the invention includes a therapeutically active agent, a pharmaceutically acceptable pH-independent polymer, and a surfactant. The pharmaceutical composition is generally prepared into an oral dosage form or a solid dosage form, such as a tablet, a capsule, a sachet, etc., and any therapeutically acceptable form.

The amount of the therapeutically active agent may be utilized at therapeutic dose levels and varies from about 5% to about 95% by weight of the pharmaceutical composition, preferably, from about 30% to about 90% by weight of the pharmaceutical composition. One example of the therapeutically active agent includes bupropion and its salts and derivatives thereof, such as bupropion hydrochloride at a concentration of about 45% to about 85% by weight. For example, about 10 mg to about 500 mg of bupropion hydrochloride can be prepared into the pharmaceutical composition of the invention. Other therapeutically active agents can also be used herein.

The therapeutically active agent can be prepared into powder, granules, particles, beads, pellets, and other pharmaceutical acceptable sizes. The therapeutically active agent can further be micronized and preferably have a particle size of less than 20 microns.

In one embodiment, the invention provides extended release formulations for the therapeutically active agent. For example, the pharmaceutical composition of the invention includes a controlled release, sustained release, or timed release dosage formulation for the therapeutically active agent. The extended release formulation as described herein can provide continuous and non-pulsating therapeutic levels of the therapeutically active agent to a mammal in need of such treatment over a period of time, such as a four-hour period or longer, a six-hour period or longer, e.g., a twelve-hour to twenty-four hour period. Such an extended release, controlled release, sustained release, or timed release dosage formulation employs a core of a pharmaceutical mixture and a coating layer. The pharmaceutical mixture contains the therapeutically active agent (e.g., bupropion hydrochloride), and the coating layer includes a pharmaceutical acceptable pH-independent polymer and a surfactant.

The core containing the therapeutically active agent generally includes a therapeutically active agent and a pharmaceutically acceptable polymer at a concentration of from about 0.01% to about 80% of the total weight of the pharmaceutical composition. The pharmaceutically acceptable polymer may help swelling or gelling of the therapeutically active agent. The pharmaceutically acceptable polymer in the core of the pharmaceutical composition may be a water-soluble polymer, a gelling polymer, such as polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, among others.

As an example, the pharmaceutically acceptable polymer to be included in the core is polyvinylpyrrolidone, such as polyvinylpyrrolidone of a high viscosity with viscosity of 55 cps or greater. Polyvinylpyrrolidone (PVP) is a linear homopolymer or copolymer having at least about 80%, preferably at least about 90% of repeat units derived from 1-vinyl-2-pyrrolidone monomers. The PVP polymer more preferably contains at least about 95% or essentially all of such repeat units and the remainder portion can be any of the various polymerization-compatible monomers, e.g., neutral monomers, such as alkenes or acrylates. Other synonyms for PVP include povidone, polyvidone, 1-vinyl-2-pyrolidinone, and 1-ethenyl-2-pyrolionone (CAS registry number 9003-39-8). PVP polymers materials are sold by various companies, including ISP Technologies, Inc. under the trademark PLASDONE™ K-29/32; BASF Aktiengesellschaf under the trademark KOLLIDON™ for USP grade PVP, for example KOLLIDON™ K-30 or K-90 (BASF Corporation, NV Division, 3000 Continental, Mount Olive, N.J. 07628-1234, USA). It is to be understood, however, that the invention is not limited to any specific PVP and that any equivalent PVP of acceptable purity, preferably pharmaceutical grade, may be used. For example, povidone can be suitably present in a total amount of from about 0.001% to about 80% by weight, such as from about 0.02% to about 50% by weight of the pharmaceutical composition.

The core of the pharmaceutical mixture may further include pharmaceutically acceptable excipients, fillers, binders and blending agents, such as hydrous or anhydrous form of lactose, starches, glucose, sucrose, mannitol, sorbitol, silicic acid, microcrystalline celluloses, sodium carboxymethylcelluloses, sodium starch glycolate, and derivatives and mixtures thereof. For example, avicel can be added into the core to a concentration of from about 0.01% to about 50% by weight of the pharmaceutical composition, such as from about 0.05% to about 40% by weight. The core of the invention may further include lubricants, blenders, anti-sticking agents, glidants, wetting agents, dyes, pigments, nonstick agents, dispersants, blenders, coating materials, and mixtures thereof, to be combined with the core of the pharmaceutical mixture. Examples of lubricants include, but are not limited to, talc, calcium stearate, magnesium stearate, glycerol monostearate, polyethylene glycols, inert silicon glass materials, colloidal silicon dioxide, and higher fatty acids and their alkali-metal and alkaline-earth-metal salts. In addition, various excipients such as diluents, lubricants, dyes, etc., which are disclosed in Remington's Pharmaceutical Sciences, 1995 Edition, may be used to optimize the pharmaceutical composition of the invention.

The amounts of the lubricants, anti-sticking agents, and other excipients generally vary from about 0.005% to about 50% by weight of the pharmaceutical composition, such as from about 0.005% to about 30%. Examples that can be blended into the core of the pharmaceutical composition include magnesium stearate, cab-O-sil, avicel, glycerol monosteartae, and talc to a final concentration of from about 1.0% to about 20% by weight of the pharmaceutical composition.

The core of the pharmaceutical mixture can be prepared in a form of granules, particles, beads, spherical beads, pellets, coated beads, coated pellets, coated particles, and other pharmaceutically acceptable shapes and sizes. This can be done by various granulation methods and other methods, such as wet and dry granulations. Wet granulation is prepared by mixing required components with various conventional well-known solvents to form granules. Alternatively, dry granulation techniques may be used to prepare the pharmaceutical composition. The mixture of the core of the pharmaceutical composition can then be incorporated into solid dosage forms, such as tablets and others, and an optional external coating is applied. For making compressed tablets, a conventional tabletting machine may be used to compress a granulated mixture of the components of the present invention into a tablet.

Embodiments of the invention provide a coating layer outside of the core containing the therapeutically active agent. The coating layer includes a pharmaceutically acceptable pH-independent polymer and a surfactant. The amount of the pharmaceutically acceptable pH-independent polymer in the coating layer of the pharmaceutical composition generally varies from about 0.01% to about 99% by weight of the coating, such as from about 5% to about 99% by weight of the coating. For example, the pharmaceutically acceptable pH-independent polymer can be used at a concentration of from about 0.001% to about 50% by weight of the pharmaceutical composition, such as from about 0.01% to about 10% by weight of the pharmaceutical composition.

The pharmaceutically acceptable pH-independent polymer includes, but is not limited to, water-insoluble polymers, water-soluble hydrophilic polymers, maltodextrin, natural gums, arabic gum, guar gum, xanthan gum, tragacanth gum, agar, gellan gum, kayara gum, alginic acids, pectins, pregelatinized starch, dextrin, maltodextrin, and blends of these polymers, and combinations thereof. Representative examples of water-insoluble polymers useful in the invention include polyacrylates, cellulose derivatives (e.g., ethylcellulose), polyvinyl acetate (e.g., Kollicoat SR30D from BASF Corporation, Mount Olive, N.J.), neutral copolymers based on ethyl acrylate and methylmethacrylate, copolymers of acrylate and methacrylates, among others. Examples of water-soluble polymers include polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and mixtures thereof.

Particularly useful pharmaceutical acceptable pH-independent polymers are those polymers with low water-permeability to delay the release of the therapeutically active agent that are suitable for controlled or sustained release formulations such that a drug or a therapeutically active agent can be released slowly and constantly whether it is under the low pH environment of the stomach or under the environment of the gastrointestinal tract. The pH-independent polymers can be in the forms of granules, powders, aqueous dispersions, and others. For example, copolymers of acrylate and methacrylates esters with quaternary ammonium groups, such as Eudragit® RS or RS30D, NE, RL or RL30D, and the like (Röhm America, LLC), are useful in preparing an extended release dosage form of bupropion.

The coating layer of the pharmaceutical composition further includes surfactants, emulsifiers, dispersing agents, defoamers, and mixtures thereof. Any of the pharmaceutically acceptable or medicinally acceptable surfactants, emulsifiers, dispersing agents, dispersants, and defoamers can be used herein and can be any of the ionic, anionic or non-ionic surfactants. For example, sodium lauryl sulfate, Tween 80 (available form Fisher Scientific International), Tween 20, Tween 100, and others can be used to a concentration of no more than 50% of the total weight, such as from about 0.01% to about 10% of the total weight. For example, a surfactant can be used in the coating layer of the pharmaceutical composition to an amount varying from about 0.001% to about 50% by weight of the coating, such as from about 0.1% to about 30% by weight of the coating. Not wishing to be bound by any theory, it is believed that the surfactant in the pharmaceutical composition enhances the channeling process of the pharmaceutical acceptable pH-independent polymer to achieve a desired drug release profile.

The coating layer may further include pharmaceutically acceptable excipients, fillers, binders and blending agents, as described above, and are disclosed in Remington's Pharmaceutical Sciences, 1995 Edition. It is found that the release rate of the therapeutically active agent can be controlled not only by incorporating suitable pharmaceutically acceptable pH-independent polymer and surfactant therein, but also by the thickness of the coating layer having excipients applied.

In one embodiment, the invention provides prolonged release formulations of bupropion hydrochloride prepared by the pharmaceutical composition of the invention, such as controlled release or extended release formulations. In an alternative embodiment, the invention provides a method for preparing an extended release formulation by preparing a core and coating the core with the coating layer. The coated core is then incorporated into solid dosage forms, such as tablets.

The pharmaceutical compositions of the invention may have an additional second coating layer containing a pharmaceutically acceptable coating mixture. The pharmaceutically acceptable coating mixture in the second coating layer includes, but is not limited to, an enteric polymer, a salt, a rapid-disintegrating coating material, a colorant, a plasticizer, a water-soluble polymer, a water-insoluble polymer, a dye, a pigment, other disintegrants, and combinations thereof. One common example of rapid-disintegrating coating material is OPADRY, available from Colorcon, Inc.

Examples of enteric polymers include methacrylic acid copolymers (e.g., Eudragit® S and Eudragit® L, available from Röhm America, LLC), hydroxypropyl methylcellulose phthalate, hydroxypropyl methylcellulose acetate, hydroxypropyl methylcellulose succinate, carboxymethylethylcellulose, cellulose acetophthalate. Generally enteric polymers rapidly disintegrate or dissolve at pH 5 or above.

Any commonly used pharmaceutically acceptable salts can be used in the second coating layer. For example, sodium chloride, magnesium choride, among others. In addition, examples of plasticizers include polyethylene glycol (PEG), propylene glycol, and others. Further, water-soluble polymers generally have a high degree of swelling in contact with water or aqueous media such as the stomach contents. Examples of water-soluble polymers include hydroxypropyl methylcellulose, hydroxypropyl cellulose, polyethylene oxide, and others. The second coating layer may further include pharmaceutically acceptable excipients, fillers, binders and blending agents, as described above and also disclosed in Remington's Pharmaceutical Sciences, 1995 Edition.

Generally, the amount of the second coating layer surrounding the coated tablet is from about 0.001% to about 5% of the total weight of the pharmaceutical composition, such as from about 0.01% to about 2% based on the total weight of the pharmaceutical composition. It is found that the release rate of the therapeutically active agent can be controlled not only by incorporating the first coating layer surrounding the bupropion containing core, but also by the thickness of the second coating layer.

In one aspect, the dosage forms of the pharmaceutical composition prepared according to the invention exhibit a desired release profile for controlled release, sustained release, or extended release formulations. The term "release" is broadly defined herein as absorption or dissolution of a compound, either in vivo or in vitro. The in vivo absorption is generally performed by measuring the plasma concentration of the therapeutically active agent over a period of time. The in vitro release profile of the therapeutically active agent can be tested in a USP type 2 apparatus at about 50 rpm in about 900 ml of phosphate buffer (pH 5) and at 37° C. Other buffers can be used herein, e.g., acetate buffer (pH 5) can be used. Any standard USP testing apparatus and conditions can be used. For example, a USP type 1 apparatus may be used at about 75 rpm under simulated intestinal buffer (SIF) or simulated gastric buffer (SGF, low pH conditions, pH is about 1.5).

In another aspect, embodiments of the invention provide a release profile of the therapeutically active agent under SIF conditions having up to about 40% release of the during the initial 2 hours, preferably from about 5% to about 40% release. The pharmaceutical composition further provides from about 10% to about 75% release of the therapeutically active agent within 4 hours, from about 30% to about 90% release of the therapeutically active agent within 6 hours, preferably from about 40% to about 80% release within 6 hours. Within 12 hours, the pharmaceutical composition provides no less than about 50% release of the therapeutically active agent, preferably no less than about 75% release.

In addition, embodiments of the invention provide a release profile of the therapeutically active agent under SGF conditions having up to about 20% release of the therapeutically active agent during the initial 2 hours, preferably from about 2% to about 20% release. The pharmaceutical composition further provides from about 10% to about 65% release of the therapeutically active agent within 4 hours, from about 30% to about 75% release of the therapeutically active agent within 6 hours, preferably from about 30% to about 75% release within 6 hours. Within 12 hours, the pharmaceutical composition provides no less than about 50% release of the therapeutically active agent, preferably no less than about 75% release.

In yet another embodiment, a method of administering an extended release pharmaceutical composition is provided. The method includes administering the pharmaceutical composition of the invention having a therapeutically active agent in an effective amount to treat a mammal. For example, an extended release formulation of bupropion hydrochloride tablet prepared according to the embodiments of the invention can be used in an effective amount of about 150 mg per day for the treatment of depression or smoke cessation, such as major depressive disorders. Initial dose of about 150 mg per day may be continued for several days. In some cases, a higher dose of about 300 mg per day may be used.

EXAMPLES

Exemplary controlled release dosage formulations are prepared and described herein. Pharmaceutical compositions having a therapeutically active agent at a concentration of from about 40% to about 80% by total weight, a pH-independent pharmaceutically acceptable polymer at a concentration of from about 0.1% to about 5% of total weight, and a surfactant at a concentration of from about 0.1% to about 4.9% of total weight are formulated and tested herein. Generally, oral dosage formulations of bupropion, such as bupropion hydrochloride, in the form of an extended release tablet are tested in vitro for their release profile and in some cases compared in vivo to healthy human subjects with a reference formulation. The reference formulation used is the Wellbutrin® XL tablet (GlaxoSmithKline).

Example 1

Bupropion hydrochloride 150 mg and 300 mg extended release tablets are prepared. Each tablet includes about 150 mg or about 300 mg of bupropion hydrochloride, povidone (USP grade) at about 0.1% to about 5% by weight, Avicell at about 0.01% to about 2% by weight, glycerol monostearate at about 0.01% to about 2% by weight, talc at about 0.001% to about 1% by weight, magnesium stearate at about 0.001% to about 1% by weight, Eudragit® RS at about 0.01% to about 2% by weight, sodium lauryl sulfate at about 0.001% to about 1% by weight, Eudragit® L at about 0.01% to about 2% by weight, sodium chloride at about 0.001% to about 0.1% by weight, and optionally an anti-sticking agent and a colorant.

Granulation: First of all, appropriate amount of povidone is dissolved in water. Bupropion hydrochloride and Avicel are placed in a vertical granulator and pre-blended for about 10 to about 20 minutes. The solution of povidone is sprayed onto the blend during the second blending. Extra water and blending time may be needed to achieve granulation consistency. The granules are then placed at about 40° C. until its moisture content (i.e., loss-on-drying at 105° C., 10 minutes) is below 1.5%. Once the drying is completed, granules are milled and mixed with glycerol monostearate, cab-O-sil, Talc, and magnesium stearate in a V-blender.

Tabletting: The resulting granule mixture is pressed into tablet cores (11/32" diameter, standard concave punch) with average hardness being between 7 and 13 Kp. These tablet cores are then coated with a coating mixture as a first coating layer.

First coating: The coating mixture for the first coating layer is prepared by first dissolving Eudragit® RS in a mixture of water and alcohol and then adding sodium lauryl sulfate. The coating mixture or dispersion is then sprayed onto the tablet cores in a coating pan (O'Harra) at about 47° C.

Second coating or color coating: The coated tablet is coated again with enteric coating Eudragit® L plus, optionally, sodium chloride, anti-sticking agents and colorants using a pan coater. Typically, a theoretical coating level of approximately 1% is obtained.

Release: The resulting tablets together with reference tablets are tested in about 900 ml acetate buffer (pH 5) according to the procedure described in United States Pharmacopeia, Apparatus 2, at a speed of about 75 rpm with paddle and found to have the following release profile. The results demonstrate an extended release of bupropion prepared by the method and formulation of example 1.

| Time (hours) | Reference % Released | Example 1 % Released |
|---|---|---|
| 0 | 0 | 0 |
| 2 | 32.82 | 24.10 |
| 4 | 56.49 | 53.40 |
| 8 | 80.27 | 84.18 |
| 14 | 90.05 | 90.85 |

Example 2

Bupropion hydrochloride 300 mg extended release tablets are prepared in the same manner as described above.

Release: The resulting tablets together with reference tablets are tested in about 900 ml acidic buffer (pH 1.5) according to the procedure described in United States Pharmacopeia, Apparatus 2, at a speed of about 75 rpm with paddle and found to have the following release profil. The results demonstrate an extended release of bupropion prepared by the method and formulation of example 2.

| Time (hours) | Reference % Released | Example 2 % Released |
|---|---|---|
| 0 | 0 | 0 |
| 2 | 8.61 | 9.72 |
| 4 | 52.87 | 51.25 |

-continued

| Time (hours) | Reference % Released | Example 2 % Released |
|---|---|---|
| 8 | 85.72 | 85.12 |
| 14 | 99.54 | 97.39 |

While the foregoing is directed to embodiments of the present invention, other and further embodiments of the invention may be devised without departing from the basic scope thereof, and the scope thereof is determined by the claims that follow.

What is claimed is:

1. An extended release pharmaceutical composition, comprising:
    a tablet core of a pharmaceutical mixture comprising bupropion;
    a first coating layer surrounding the tablet core, the first coating layer comprising: a pharmaceutically acceptable pH-independent polymer; and sodium lauryl sulfate; and a second coating layer surrounding the first coating layer, the second coating layer comprising: a pharmaceutically acceptable coating mixture, wherein the coating mixture comprises an enteric polymer.

2. The extended release pharmaceutical composition of claim 1, wherein the second coating layer is from 0.001% to 5% of the total weight of the pharmaceutical composition.

3. The extended release pharmaceutical composition of claim 2, wherein the second coating layer is from 0.01% to 2% of the total weight of the pharmaceutical composition.

4. The extended release pharmaceutical composition of claim 1, wherein the second coating layer comprises methacrylic acid copolymers.

5. The extended release pharmaceutical composition of claim 4, wherein the second coating layer further comprises sodium chloride, anti-sticking agents, and colorants.

6. The pharmaceutical composition of claim 1, wherein the pharmaceutical composition comprises from 5% to 95% by weight of a bupropion salt, from 0.01% to 50% by weight of a pH-independent polyacrylate polymer, and from 0.001% to 30% by weight of a sodium lauryl sulfate.

7. The pharmaceutical composition of claim 1, wherein the enteric polymer is a polymer selected from the group consisting of a cellulose acetate phthalate, a cellulose phthalate hydroxy propyl methyl ether, a polyvinyl acetate phthalate, a hydroxy propyl methyl cellulose acetate succinate, a cellulose acetate trimellitate, a shellac, a polyacrylate polymer, methacrylic acid copolymers, and combinations thereof.

8. The extended release pharmaceutical composition of claim 1, wherein the bupropion comprises from about 10 mg to about 500 mg of bupropion hydrochloride.

9. The extended release pharmaceutical composition of claim 1, wherein the pharmaceutically acceptable pH-independent polymer is a polymer selected from the group consisting of copolymers of acrylate and methacrylate esters with quaternary ammonium groups, and combinations thereof.

* * * * *